United States Patent
Nabutovsky et al.

(10) Patent No.: US 9,713,494 B2
(45) Date of Patent: *Jul. 25, 2017

(54) FEEDBACK SYSTEMS AND METHODS FOR RENAL DENERVATION UTILIZING BALLOON CATHETER

(71) Applicant: St. Jude Medical, Cardiology Division, INc., St. Paul, MN (US)

(72) Inventors: Yelena Nabutovsky, Sunnyvale, CA (US); Edward Karst, Los Angeles, CA (US); Fujian Qu, San Jose, CA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/219,991

(22) Filed: Jul. 26, 2016

(65) Prior Publication Data

US 2016/0331451 A1    Nov. 17, 2016

Related U.S. Application Data

(60) Continuation of application No. 15/063,600, filed on Mar. 8, 2016, now Pat. No. 9,427,283, which is a
(Continued)

(51) Int. Cl.
*A61B 18/18*    (2006.01)
*A61B 18/14*    (2006.01)
(Continued)

(52) U.S. Cl.
CPC ........ *A61B 18/1492* (2013.01); *A61B 5/0215* (2013.01); *A61B 5/6853* (2013.01);
(Continued)

(58) Field of Classification Search
CPC ...... A61B 18/1492; A61B 2018/00773; A61B 2018/0022; A61B 2018/00434;
(Continued)

(56) References Cited

U.S. PATENT DOCUMENTS 3,650,277 A    3/1972    Sjostrand et al.
4,658,819 A    4/1987    Harris et al.
(Continued)

FOREIGN PATENT DOCUMENTS

WO    97/45157    12/1997
WO    00/66020    11/2000
(Continued)

OTHER PUBLICATIONS

Abboud, Francois M., The Sympathetic System in Hypertension, State-of-the-Art Review, Hypertension Journal of the American Heart Association, Hypertension 4 (suppl II): II-208-II-225, 1982.
(Continued)

*Primary Examiner* — Rex R Holmes
(74) *Attorney, Agent, or Firm* — Armstrong Teasdale LLP

(57) ABSTRACT

A renal denervation system includes an ablation catheter and an inflation balloon. The renal denervation catheter is insertable into a renal artery to perform a renal denervation procedure. The inflation balloon is inflatable within the renal artery, wherein one of a blood pressure condition in the renal artery resulting from operation of the inflation balloon and a performance characteristic of the inflation balloon indicates efficacy of the renal denervation procedure.

18 Claims, 7 Drawing Sheets

Related U.S. Application Data division of application No. 14/868,455, filed on Sep. 29, 2015, now Pat. No. 9,314,300, which is a division of application No. 13/836,193, filed on Mar. 15, 2013, now Pat. No. 9,179,973.

(51) Int. Cl.
- *A61B 5/0215* (2006.01)
- *A61B 5/00* (2006.01)
- A61B 18/00 (2006.01)
- A61B 90/00 (2016.01)

(52) U.S. Cl.
CPC ...... *A61B 18/18* (2013.01); *A61B 2018/0022* (2013.01); *A61B 2018/00267* (2013.01); *A61B 2018/00285* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61B 2018/00744* (2013.01); *A61B 2018/00761* (2013.01); *A61B 2018/00773* (2013.01); *A61B 2018/00863* (2013.01); *A61B 2090/064* (2016.02)

(58) Field of Classification Search
CPC  A61B 2018/00404; A61B 2018/00642; A61B 2018/00577; A61B 2018/00505
See application file for complete search history.

(56) References Cited

U.S. PATENT DOCUMENTS

| | | | |
|---|---|---|---|
| 5,035,694 A | 7/1991 | Kasprzyk et al. | |
| 5,255,679 A | 10/1993 | Imran | |
| 5,300,068 A | 4/1994 | Rosar et al. | |
| 5,368,591 A | 11/1994 | Lennox et al. | |
| 5,387,233 A | 2/1995 | Alferness et al. | |
| 5,464,717 A | 11/1995 | Sakaguchi et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Mulier et al. | |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,012,475 A | 1/2000 | Taylor et al. | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 9,427,283 B2 * | 8/2016 | Nabutovsky | A61B 18/18 |
| 9,439,598 B2 | 9/2016 | Shimada et al. | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2005/0288730 A1 | 12/2005 | Deem et al. | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2010/0016762 A1 | 1/2010 | Thapliyal et al. | |
| 2010/0094209 A1 | 4/2010 | Drasler et al. | |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0208173 A1 | 8/2011 | Sobotka et al. | |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0172870 A1 | 7/2012 | Jenson et al. | |
| 2012/0232409 A1 * | 9/2012 | Stahmann | A61B 5/201 |
| | | | 600/483 |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |

(56) References Cited

FOREIGN PATENT DOCUMENTS

| WO | 03/082080 | 10/2003 |
|---|---|---|
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/075156 | 6/2012 |
| WO | 2012/106492 | 8/2012 |
| WO | 2012/158864 | 11/2012 |

OTHER PUBLICATIONS

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.

Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.

Badoer, Emilio et al, Cardiac Afferents Play the Dominant Role in Renal Nerve Inhibition Elicited by Volume Expansion in the Rabbit, American Journal of Physiology, 1998, R383-R388.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.

Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.

Barajas, Luciano et al, Monoaminergic Innervation of the Rat Kidney: A Quantitative Study, American Journal of Physiology, vol. 259, No. 3, Sep. 1990, F503-F511.

Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.

Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.

Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.

Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.

Bertog, Stefan C. et al, Renal Denervation for Hypertension, JACC: Cardiovascular Interventions, vol. 5, No. 3, Mar. 2012, 249-258.

Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.

Blankestijn, Peter J. et al, Renal Denervation: Potential Impact on Hypertension in Kidney Disease?, Nephrol Dial Transplant (2011) 0: 1-3.

Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.

Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

Brookes, Linda et al, Renal Denervation: Is Reality Meeting Expectations?, An Interview with Michel Azizi, MD, PhD, Medscape, Jan. 7, 2013.

Bunte, Matthew C. et al, Endovascular Treatment of Resistant and Uncontrolled Hypertension, JACC: Cardiovascular Interventions, vol. 6, No. 1, Jan. 2013, 1-9.

Calleary, Hickey D. et al, Pre-Transplant Bilateral Native Nephrectomy for Medically Refractory Hypertension, The Irish Medical Journal, Jul.-Aug. 2001;94(7):214-6.

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

Campese, V.M., Is Hypertension in Chronic Renal Failure Neurogenic in Nature?, Nephrol Dial Transplant, 1994, 9: 741-742.

Campese, Vito M. et al, Neurogenic Factors in Renal Hypertension, Current Hypertension Reports, 2002 4: 256-260.

Campese, Vito M. et al, Renal Afferent Denervation Prevents Hypertension in Rats With Chronic Renal Failure, Hypertension, 1995, 25, 878-882.

Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.

Campese, Vito M., Interventional Hypertension: A New Hope or a New Hype? The Need to Redefine Resistant Hypertension, J Hypertens. Nov. 2013; 31(11):2118-21.

Canadian Agency for Drugs and Technologies in Health, Catheter-Based Renal Denervation for Treatment-Resistant Hypertension; Issues in Emerging Health Technologies, Issue 121, Mar. 2013.

Carlstedt, Thomas et al, Regrowth of Lesioned Dorsal Root Nerve Fibers into the Spinal Cord of Neonatal Rats, Neuroscience Letters Feb. 10, 1987;74(1):14-8.

Chabanier, H. et al, On the Decapsulation and Neurectomy of the Kidnesy in Permanent Hypertensive States, The Medical Press, Feb. 22, 1936, No. 16, 307-310.

Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.

Ciriello, John et al, Renal Afferents and Hypertension, Current Hypertension Reports 2002, 4:136-142.

Converse, Richard L. et al, Sympathetic Overactivity in Patients with Chronic Renal Failure, The New England Journal of Medicine, vol. 327, No. 27, 1992, 1912-1918.

Crile, George, The Clinical Results of Celiac Ganglionectomy in the Treatment of Essential Hypertension, Annals of Surgery, Jun. 1938; 107(6): 909-916.

Cruickshank, J.M., Beta-Blockers Continue to Surprise Us, European Heart Journal (2000) 21, 354-364.

Curtis, John J. et al, Surgical Therapy for Persistent Hypertension After Renal Transplantation, Transplantation, vol. 31, No. 2, 1981, 125-128.

Dailey, U.G., Surgical Treatment of Hypertension: A Review—Part II, Journal of the National Medical Association, May 1948, vol. 40, No. 3, 113-116.

Dailey, U.G., Surgical Treatment of Hypertension: A Review—Part III, Journal of the National Medical Association, Jul. 1948, vol. 40, No. 4, 160-162.

(56) References Cited

OTHER PUBLICATIONS

Dailey, U.G., The Surgical Treatment of Hypertension: A Review, Journal of the National Medical Association, Mar. 1948, vol. 40, No. 2, 76-79.

Davis, Mark I. et al, Effectiveness of Renal Denervation Therapy for Resistant Hypertension A Systematic Review and Meta-Analysis, Journal of the American College of Cardiology, vol. 62, No. 3, Jul. 16, 2013, 231-241.

De Wardener, H.E., The Hypothalamus and Hypertension, Physiological Reviews,vol. 81, No. 4, Oct. 2001.

Dequattro V. et al, The Sympathetic Nervous System: The Muse of Primary Hypertension, Journal of Human Hypertension, 2002, 16 (Suppl 1), S64-S69.

DiBona, Gerald F. et al, Neural Control of Renal Function, Physiological Reviews, vol. 77, No. 1, Jan. 1997, 75-197.

DiBona, Gerald F. et al, Translational Medicine: The Antihypertensive Effect of Renal Denervation, Americal Journal of Physiology, 2010, 298, R245-R253.

DiBona, Gerald F., Neural Control of Renal Function: Cardiovascular Implications, Hypertension Journal of The American Heart Association, vol. 13, No. 6, Part 1, Jun. 1989, 539-548.

DiBona, Gerald F., Neural Control of the Kidney: Functionally Specific Renal Sympathetic Nerve Fibers, American Journal of Physiology, 2000, 279, R1517-R1524.

DiBona, Gerald F., Neural Control of the Kidney: Past, Present, and Future, Hypertension Journal of The American Heart Association, vol. 41, Mar. 2003, Part II, 621-624.

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013; Nov. 28, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; Mar. 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of The American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oparil, Suzanne et al, Renal Nerve Ablation: Emerging Role in Therapeutics; Blood Pressure, Oct. 2011, vol. 20, No. 5, pp. 253-255.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, TIME Magazine, Monday, Jan. 9, 2012.

Page, Irvine H. et al, Mechanisms, Diagnosis and Treatment of Hypertension of Renal Vascular Origin, Annal of Internal Medicine, Aug. 1959, vol. 51, No. 2, 196-211.

Page, Irvine H. et al, Mechanisms, Diagnosis and Treatment of Hypertension of Renal Vascular Origin; Annals of Internal Medicine, Aug. 1959;51:196-211.

Page, Irvine H. et al, The Effect of Renal Denervation on the Level of Arterial Blood Pressure and Renal Function in Essential Hypertension, Journal of Clinical Investigation, 1935;14(1):27-30.

Page, Irvine H. et al, The Effects of Renal Denervation on Patients Suffering from Nephritis, J Clin Invest. 1935;14 (4):443-458.

Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

Page, Max, Section of Surgery, Discussion on the Surgical Treatment of Hypertension, Proceedings of the Royal Society of Medicine, vol. XLI, Feb. 1948, 359-372.

Papademetriou, Vasilios, Hypertension and the Simplicity Renal Denervation System, Scientific Background, www.medtronic.com, 2011.

Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

(56) References Cited

OTHER PUBLICATIONS

Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, , Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention, May 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.

(56) References Cited

OTHER PUBLICATIONS

Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Zazgornik, Jan et al, Bilateral Nephrectomy: The Best, but Often Overlooked, Treatment for Refractory Hypertension in Hemodialysis Patients, AJH 1998; 11:1364-1370.
DiBona, Gerald F., Renal Innervation and Denervation: Lessons from Renal Transplantation Reconsidered, Artificial Organs, vol. 11, No. 6, 1987, 457-462.
DiBona, Gerald F., Role of the Renal Nerves in Renal Sodium Retention and Edema Formation, Trans Am Clin Climatol Assoc. 1990; 101: 38-45.
DiBona, Gerald F., Sympathetic Nervous System and Hypertension, Hypertension Journal of The American Heart Association, Jan. 28, 2013; 61: 556-560.
DiBona, Gerald F., Sympathetic Nervous System and the Kidney in Hypertension, Curr Opin Nephrol Hypertens. Mar. 2002;11(2):197-200.
DiBona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. Jul. 8, 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

(56) References Cited

OTHER PUBLICATIONS

Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: the Converge Report, Heart, Sep. 15, 2013; 0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, Nov. 8, 2013; 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 mailed Jan. 3, 2011.
International Search Report and Written Opinion for Application No. PCT/US2010/054684 mailed Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19-26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339; Feb. 2013.
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

(56) References Cited

OTHER PUBLICATIONS

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After Symplicity HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.

Mahfoud, Felix et al, Expert Consensus Document from the European Society of Cardiology on Catheter-Based Renal Denervation, European Heart Journal, Apr. 25, 2013; 34(28):2149-57.

Mancia, Giuseppe et al, Sympathetic Activation in the Pathogenesis of Hypertension and Progression of Organ Damage, Hypertension Journal of the American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter-based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65, 729-734.

\* cited by examiner

FEEDBACK SYSTEMS AND METHODS FOR RENAL DENERVATION UTILIZING BALLOON CATHETER

This application is a continuation application of U.S. patent application Ser. No. 15/063,600, filed on Mar. 8, 2016, which is a divisional application of U.S. patent application Ser. No. 14/868,455, filed on Sep. 29, 2015, and issued as U.S. Pat. No. 9,314,300, which is a divisional application of U.S. patent application Ser. No. 13/836,193 filed on Mar. 15, 2013, and issued as U.S. Pat. No. 9,179,973, the entire contents of which are hereby incorporated herein by reference in their entirety.

TECHNICAL FIELD

The present disclosure relates generally to renal denervation system and methods, and more particularly, to systems and methods for assessing the efficacy of a renal denervation procedure intraoperatively.

BACKGROUND

Renal denervation is a method whereby sympathetic nerve activity involving the targeted kidney is blocked or suppressed. Excessive sympathetic activity has been implicated in vasoconstriction, reduction in renal blood flow, retention of fluid and salt, elevated renin generation, over-activation of the renin-angiotension-aldosterone mechanism, increased catecholamine production and, ultimately, arterial hypertension. Thus, renal denervation is used to alter neural signaling mechanisms involving the kidney to treat hypertension and other related disorders.

Renal denervation is achieved through destruction of afferent and efferent nerve fibers that run adjacent to the renal arteries. Successful renal denervation results in lower systemic arterial blood pressure in a treated patient. Renal denervation has also been shown to have benefits in conjunction with current guideline-based treatment strategies in heart failure, diabetes, obesity, sleep apnea, and ventricular tachycardia (VT). A conventional renal denervation procedure involves introducing a radiofrequency (RF) ablation catheter, which ablates renal nerves at various locations using variable energy. Ideally, the operator's objective is to ablate as minimally as necessary to achieve an appropriate degree of renal denervation for the least amount of time and at the fewest locations. In order to achieve it, there is a need for feedback mechanisms to provide the operator with insight about the efficacy of the renal denervation treatment during the treatment procedure. This feedback would enable the operator to decide whether additional power, duration, and/or ablation locations are needed to accomplish adequate renal denervation.

SUMMARY

One aspect of the present disclosure relates to a renal denervation system, which includes a renal ablation catheter and an inflation balloon. The renal ablation catheter is insertable into a renal artery to perform a renal denervation procedure. The inflation balloon is inflatable within the renal artery, wherein a blood pressure condition in the renal artery resulting from operation of the inflation balloon and a performance characteristic of the inflation balloon indicates the efficacy of the renal denervation procedure.

The inflated balloon may block blood flow through the renal artery temporarily, and the blood pressure condition is assessed at a location distal of the inflation balloon (e.g., between the inflation balloon and the kidney) with a blood pressure measurement sensor. The blood pressure condition may be measured before and after ablating the renal artery in order to detect if there is a change in blood pressure condition. The blood pressure condition assessment includes a rate of decay of the blood pressure after blood occlusion due to balloon inflation. Another blood pressure condition assessment includes a time period required to inflate the inflation balloon. The time period required to inflate the balloon to reach a pressure threshold may relate to the degree of vasodilation in the renal artery. The renal denervation catheter and the inflation balloon may be separately insertable into the renal artery.

Another aspect of the present disclosure relates to a method of determining efficacy of a renal denervation procedure in a renal artery. The method includes providing a renal denervation catheter and a inflation balloon, filling the inflation balloon within the renal artery to stop blood flow and measuring one of a blood pressure condition in the renal artery and a performance characteristic of the inflation balloon prior to performing the renal denervation procedure to obtain a first measurement, then filling the inflation balloon within the renal artery to stop blood flow and measuring the one of a blood pressure condition in the renal artery and a performance characteristic of the inflation balloon after performing the renal denervation procedure to obtain a second measurement, and comparing the first and second measurements to determine the efficacy of the renal denervation procedure.

The blood pressure condition may include a decay of the blood pressure condition upon deflating the inflation balloon. Measuring the blood pressure condition may include positioning a pressure sensor distal of the balloon (e.g., between the inflation balloon and the kidney). The performance characteristic of the inflation balloon may include an inflation rate of the inflation balloon. The performance characteristic of the inflation balloon may include an amount of time to inflate the inflation balloon to a predetermined pressure level. A reduction in the amount of time may correlate with unloading of sympathetic tone from the renal artery.

A further aspect of the present disclosure relates to a method of determining the efficacy of a renal denervation procedure in a renal artery. The method includes providing a renal denervation catheter and a inflation balloon, measuring a first amount of time to fill the inflation balloon within the renal artery, performing a first renal denervation procedure in the renal artery with the renal denervation catheter, after performing the first renal denervation procedure, measuring a second amount of time to fill the inflation balloon within the renal artery, and comparing the first and second amounts of time to determine the efficacy of the first renal denervation procedure.

Filling the inflation balloon may include filling the inflation balloon to a predetermined pressure level. The method may include axially moving the renal denervation catheter within the renal artery, performing a second renal denervation procedure, after performing the second renal denervation procedure, measuring a third amount of time to fill the inflation balloon, and comparing the third amount of time to at least one of the first and second amounts of time to determine efficacy of the second renal denervation procedure.

Another aspect of the present disclosure relates to a method of determining efficacy of a renal denervation procedure in a renal artery. The method includes providing a renal denervation catheter and a inflation balloon, inflating the inflation balloon to block blood flow through the renal artery and measuring a first rate of decay of blood pressure in the renal artery, deflating the inflation balloon, performing a first renal denervation procedure in the renal artery with the renal denervation catheter, after performing the renal denervation procedure, inflating the inflation balloon to block blood flow through the renal artery and measuring a second rate of decay of blood pressure in the renal artery, and comparing the first and second rates of decay of blood pressure to determine efficacy of the first renal denervation procedure.

The renal denervation catheter may include a plurality of ablation members, and the method may include positioning the inflation balloon distal of the plurality of ablation members prior to filling the inflation balloon. The method may include providing the renal denervation catheter and inflation balloon on a common delivery device. The method may include performing a second renal denervation procedure after comparing the rates of decay of blood pressure, after performing the second renal denervation procedure, filling the inflation balloon to block blood flow through the renal artery and measuring a third rate of decay of blood pressure in the renal artery, and comparing the third rates of decay of blood pressure with at least one of the first and second rates of decay of blood pressure to determine efficacy of the second renal denervation procedure.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

Figure 1:
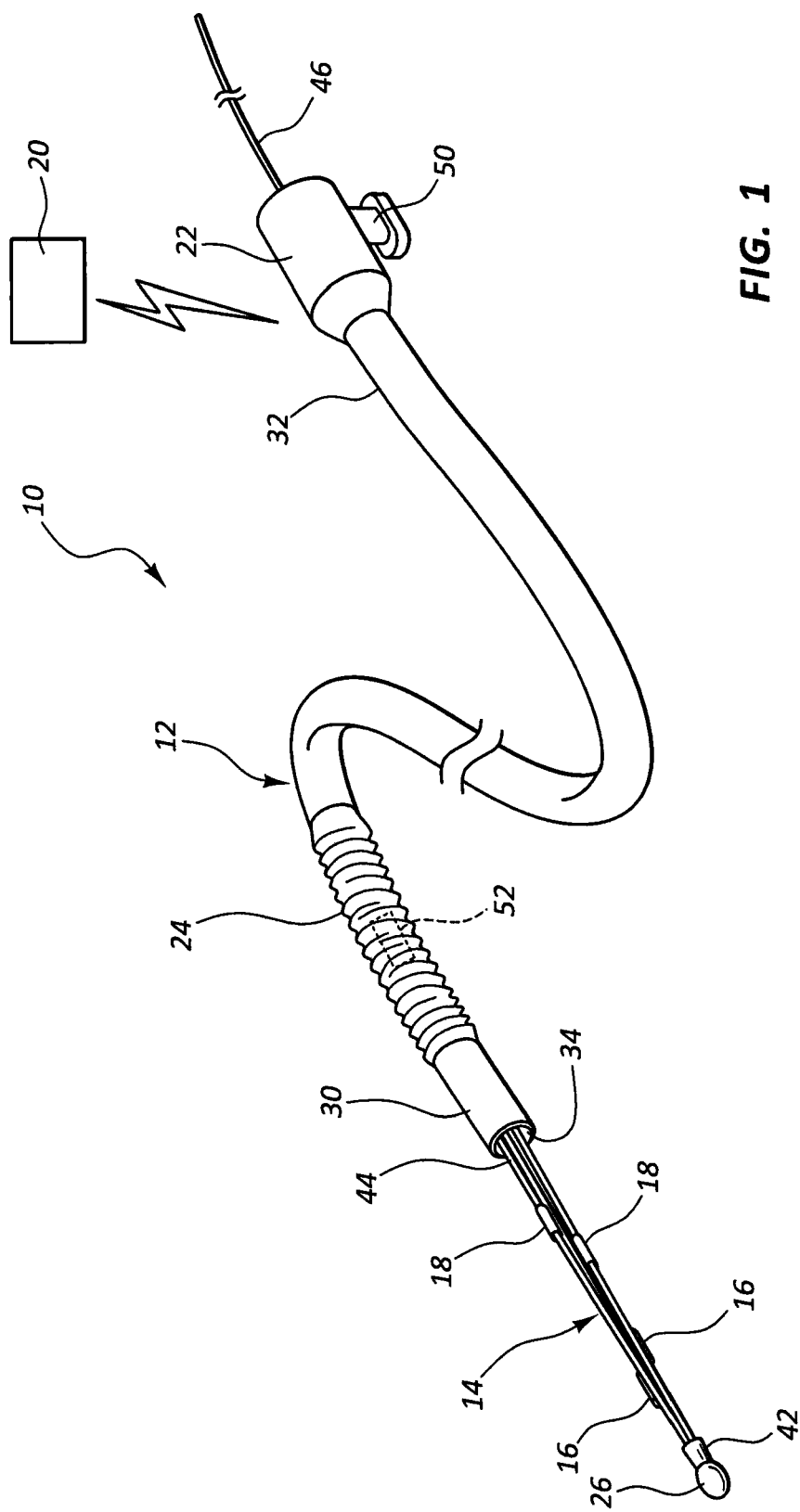
FIG. 1 is a perspective view of an example renal denervation catheter in accordance with the present disclosure.

The systems and methods disclosed herein are directed to aspects of renal denervation in a patient. The principles disclosed herein may be applicable to other systems and methods used for treating other aspects of the body, including, for example, any portion of the gastrointestinal, cardiovascular, nervous, hormonal, respiratory, excretory and reproductive systems of the body.

Renal denervation includes ablation of the renal artery using an ablation catheter. While not meant to be limiting, the systems and methods disclosed herein are used to provide feedback to an operator concerning the efficacy of the renal denervation procedure. The feedback may be given during the procedure, such as after ablating the renal artery while the ablation catheter remains positioned within the renal artery. It will be appreciated that the systems and methods discloses herein may be applicable to other ablation procedures that disrupt innervation.

The general structure and function of renal denervation catheters (also referred to as renal ablation catheters) used for ablating tissue in the renal artery are well known in the art. The principles disclosed herein may be useful in conjunction with various renal denervation catheters and methods of conducting renal denervation procedures. One procedure for renal denervation includes introducing a radio frequency ablation catheter into the renal artery and ablating renal nerves at several locations using variable energy up to, for example, about 8 Watts. The locations may be determined by a plurality of pre-positioned ablation members arranged in contact with an interior surface of the renal artery at various axially and circumferentially spaced apart locations. In other examples, a single ablation member is moved to a plurality of positions within the renal artery to ablate the renal nerves. Typically, the renal denervation procedure includes inserting the ablation catheter into the aorta retrograde to the junction with the renal artery, and then advanced the ablation catheter into the renal artery. The anatomic terms "distal" (meaning further into the renal artery) and "proximal" (meaning less far into the renal artery) are used herein to describe relative positions within the renal artery.

The renal denervation catheters of the present disclosure may provide feedback mechanisms for determining the efficacy of the procedure while the procedure is ongoing, or at least while the renal denervation device is positioned within the patient. In one example, the feedback mechanism includes determining a rate of blood flow or a change in blood flow rate through the renal artery and correlating attributes of the blood flow to efficacy of the procedure. The feedback mechanisms may provide real-time feedback to an operator while a renal denervation catheter is positioned within the renal artery. The feedback mechanism may provide information to the operator prior to and after each ablation takes place. For example, the renal denervation catheter may be positioned at one axial location along the length of the renal artery where a first set of ablations of the denervation procedure occur. The feedback mechanism may provide feedback to the operator concerning the efficacy of the first set of ablations. If the feedback indicates that insufficient ablation has occurred, the operator may move the renal denervation catheter in an axial direction along the length of renal artery and perform a second set of ablations, or may leave the renal denervation catheter in the same location and apply additional energy for further ablation. The feedback mechanism may provide additional feedback concerning efficacy of the second set of ablations. Thereafter, the operator may determine whether any additional ablation may be needed.

The renal denervation devices and methods disclosed herein utilize an inflation balloon, which is operable within the renal artery to temporarily stop blood flow without causing adverse hemodynamic effects. The inflation balloon may be an independent unit insertable into the renal artery. Alternatively, the balloon may be embedded in the body of the ablation catheter or in the body of a delivery catheter for the procedure. In a first method, a pressure sensor is positioned distal or downstream of the balloon (e.g., between the balloon and the kidney) to monitor blood pressure. After the balloon is inflated, the pressure sensor measures the decrease in blood pressure as blood passes to the glomerular apparatus and tubules of the kidney. This decrease in blood pressure may be referred to as pressure decay or exponential decay of blood pressure. Determinants of the exponential decay of blood pressure when the inflation balloon is inflated include the resistance of small arterioles and capillaries of the kidney, which prevents immediate outflow of all blood and capacitance of the renal artery and tributaries, which deflate as pressure is reduced. These two properties may be estimated using the profile of decaying blood pressure when the inflation balloon is inflated. Material properties of the vessels are unlikely to change over a short time scale, so the one way to alter the shape of the exponential decay is by altering renal vascular resistance, which is maintained under neural control. One purpose of the ablation is to relax renal vascular resistance, and may be titrated by measuring the change in the time constant of the exponential curve, which is typically directly proportional to the renal vascular resistance. A change in renal vascular resistance may be calculated by comparing time constant of exponential decay curve before and after ablation. The blood pressure measured before and after inflating the balloon may be plotted on a first graph. An increase in the rate of blood pressure decay may be used as a marker of successful denervation.

The balloon may then be deflated and the patient may be treated with at least one ablation member as part of a denervation procedure. Thereafter, the operator may reinflate the balloon and again measure the pressure decay. The pressure decay may be plotted on a second graph. Differences in the pressure decay before and after the denervation procedure may correspond to efficacy of the ablation.

A successful ablation typically reduces sympathetic vessel tone distal or downstream (e.g., toward the kidney) of the ablation site. The reduction in sympathetic vessel tone tends to decrease resistance to renal blood flow, which brings about a more rapid decrease in blood pressure downstream of the inflated balloon. Comparing the rate of pressure decrease before and after the denervation procedure may provide a reasonable indication of the success of the denervation procedure. The operator may then determine whether additional ablation is needed. The pressure decay may be measured after each ablation.

In another example method, the balloon positioned within the renal artery is inflated to a predetermined pressure level. The time required to obtain the pressure level within the balloon may correlate to sympathetic tone in the renal artery. A renal artery that has been treated with a denervation procedure typically has less sympathetic tone, thereby permitting the balloon to inflate at a faster rate to reach the predetermined pressure level. Comparing the amount of time required to inflate the balloon to a desired pressure level prior to and after a denervation procedure may provide an indication to the operator of the efficacy of the renal denervation procedure. The operator may determine, based at least in part on feedback related to the change in the amount of time required to inflate the balloon, whether additional ablation is needed. A shortening of balloon inflation time may be used as a marker of successful denervation. The balloon may be inflated after each set of ablations to provide additional feedback to the operator concerning the efficacy of the denervation procedure.

In the examples described above, the inflation balloon may be integrated into a renal denervation catheter. Alternatively, the balloon may be carried by a separate balloon catheter that is operable independent of the denervation catheter. The balloon catheter may be advanced and withdrawn within the renal artery and relative to the denervation catheter as needed in order to obtain the desired feedback prior to and after performing ablation with the denervation catheter.

Figure 2:
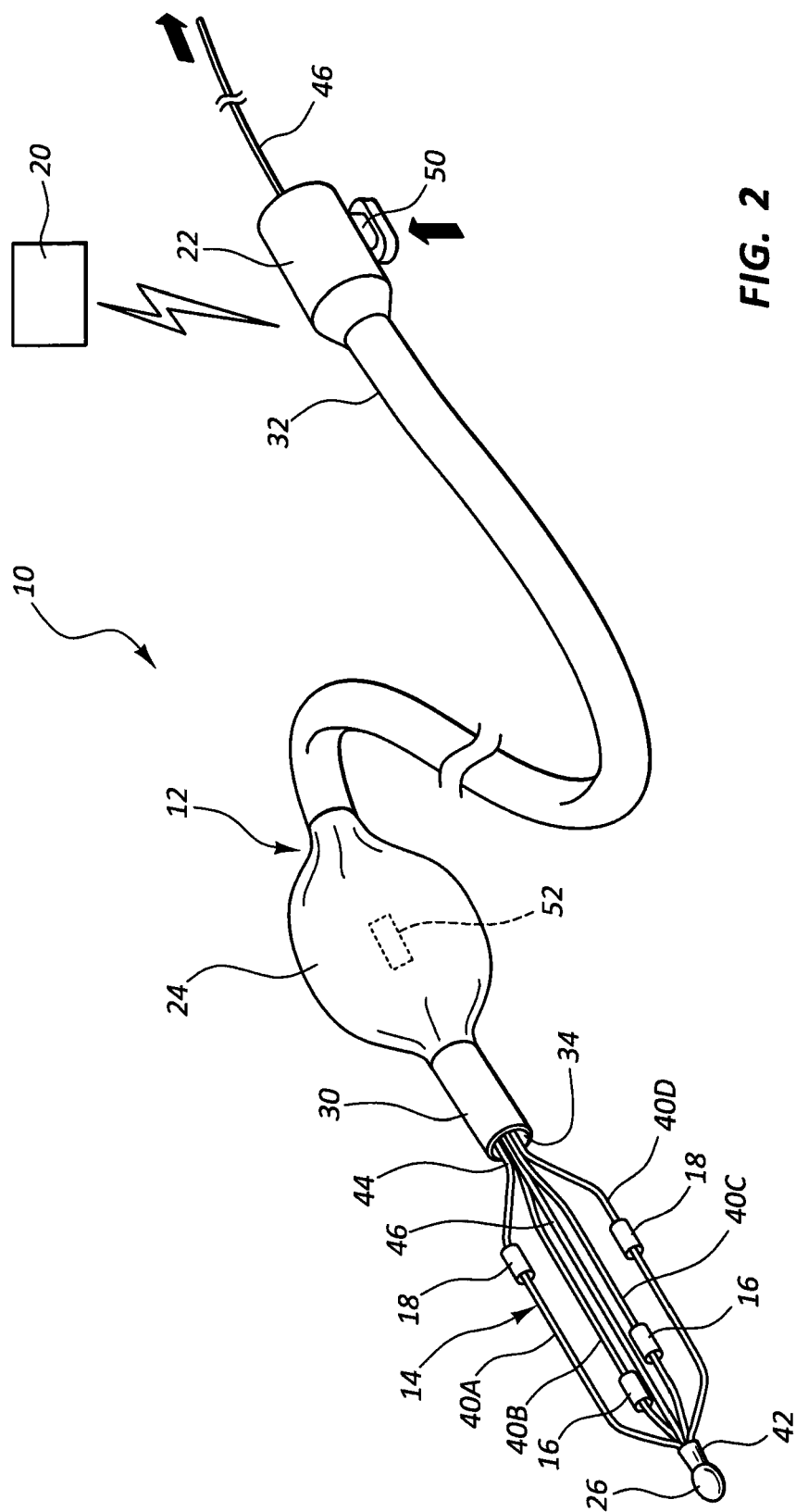
FIG. 2 is a perspective view of the renal denervation catheter of FIG. 1 in a deployed position.

Referring now to FIGS. 1 and 2, an example renal denervation catheter 10 is shown including a catheter shaft 12, a deployable basket 14, ablation electrodes 16, 18, a controller 20, a hub 22, a balloon 24, and a pressure sensor 26. The deployable basket 14 is positioned at a distal end of the catheter shaft 12. The ablation electrodes 16, 18 are mounted to the deployable basket 14. The hub 22 is positioned at a proximal end of the catheter shaft 12. The balloon 24 may be mounted directly to the catheter shaft, such as at a proximal end portion of the catheter shaft 12. The pressure sensor 26 is typically positioned distal of the balloon 24, such as at a distal tip of the deployable basket 14.

The catheter shaft 12 includes distal and proximal ends 30, 32, and a lumen 34. The deployable basket 14 includes a plurality of splines 40A-D, distal and proximal ends 42, 44, and a pull wire 46. The pull wire 46 may extend through the lumen 34 of the catheter shaft 12. Applying an axially force to the pull wire 46 may move the deployable basket 14 from a retracted position as shown in FIG. 1 to a deployed position as shown in FIG. 2.

The ablation electrodes 16, 18 may be mounted individually to the splines 40A-D. The ablation electrodes 16 may be referred to as distal electrodes and the ablation electrodes 18 may be referred to as proximal electrodes. The ablation electrodes 16, 18 are typically spaced apart axially along the length of the renal denervation catheter 10 and positioned spaced apart circumferentially when the deployable basket 14 is in a deployed position of FIG. 2. Many other arrangements are possible for the deployable basket 14 and ablation electrodes carried thereon. Different numbers of ablation electrodes and different numbers of splines may be used in other embodiments.

The ablation electrodes 16, 18 may include radio frequency (RF) electrodes. In other embodiments, the ablation electrodes 16, 18 may include other types of energy sources such as, for example, ultrasound, laser, cryothermal, and microwave energy sources.

The controller 20 may communicate with various features of the renal denervation catheter 10 such as, for example, the ablation electrodes 16, 18. The controller 20 may control the amount of energy delivered to the ablation electrodes 16, 18, the on/off state of the ablation electrodes 16, 18, and collect data provided by the ablation electrodes 16, 18 such as, for example, a temperature reading or a power level. The controller 20 may be electrically coupled to the ablation electrodes 16, 18 and other features such as, for example, the pressure sensor 26.

Figure 8:
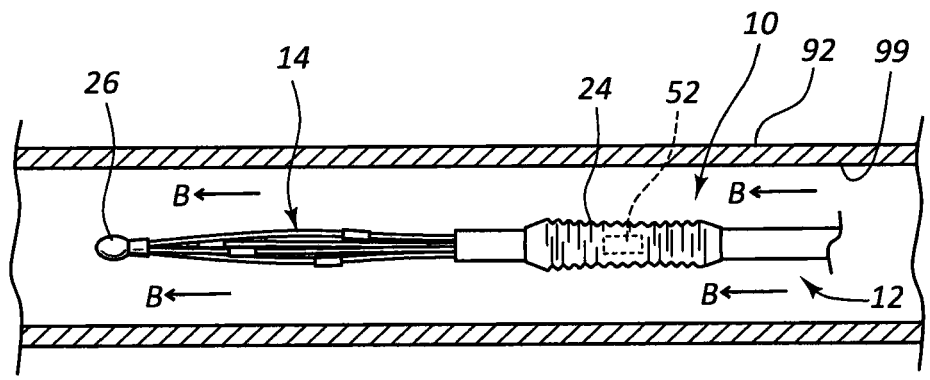
FIG. 8 shows the renal denervation catheter of FIG. 7 with the balloon deflated.
Figure 9:
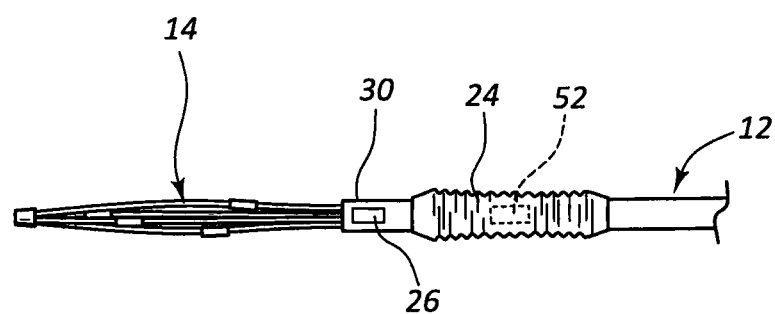
FIG. 9 shows another example renal denervation catheter in accordance with the present disclosure.

The pressure sensor 26 may be mounted at any location distal of the balloon 24. The pressure sensor 26 may be mounted to the deployable basket 14. In the example of FIGS. 1-8, the pressure sensor 26 is mounted to the distal end 42 of the deployable basket 14. FIG. 9 shows another example in which the pressure sensor 26 is mounted to the distal end 30 of the catheter shaft 12.

The hub 22 may include a pass-through opening that is connected in fluid communication with lumen 34 of the catheter shaft 12. The pull wire 46 may extend through the hub 22 where the pull wire 46 is exposed for operation by the operator. The pull wire 46 may be coupled to an actuating member (not shown) such as, for example, a lever or trigger that provides easier operation. The hub 22 may also include an inflation port 50. The inflation port 50 may be connected to a source of inflation fluid, which is delivered to the balloon 24. In at least some examples, the catheter shaft 12 includes a dedicated inflation lumen coupled in fluid communication with the balloon 24 and the inflation port 50. In other examples, the inflation fluid flows through the lumen 34. The lumen 34 includes sealing members that provide a sealed connection with the pull wire 46 to limit fluid flow out through the distal and proximal ends of the catheter shaft 12.

Figure 3:
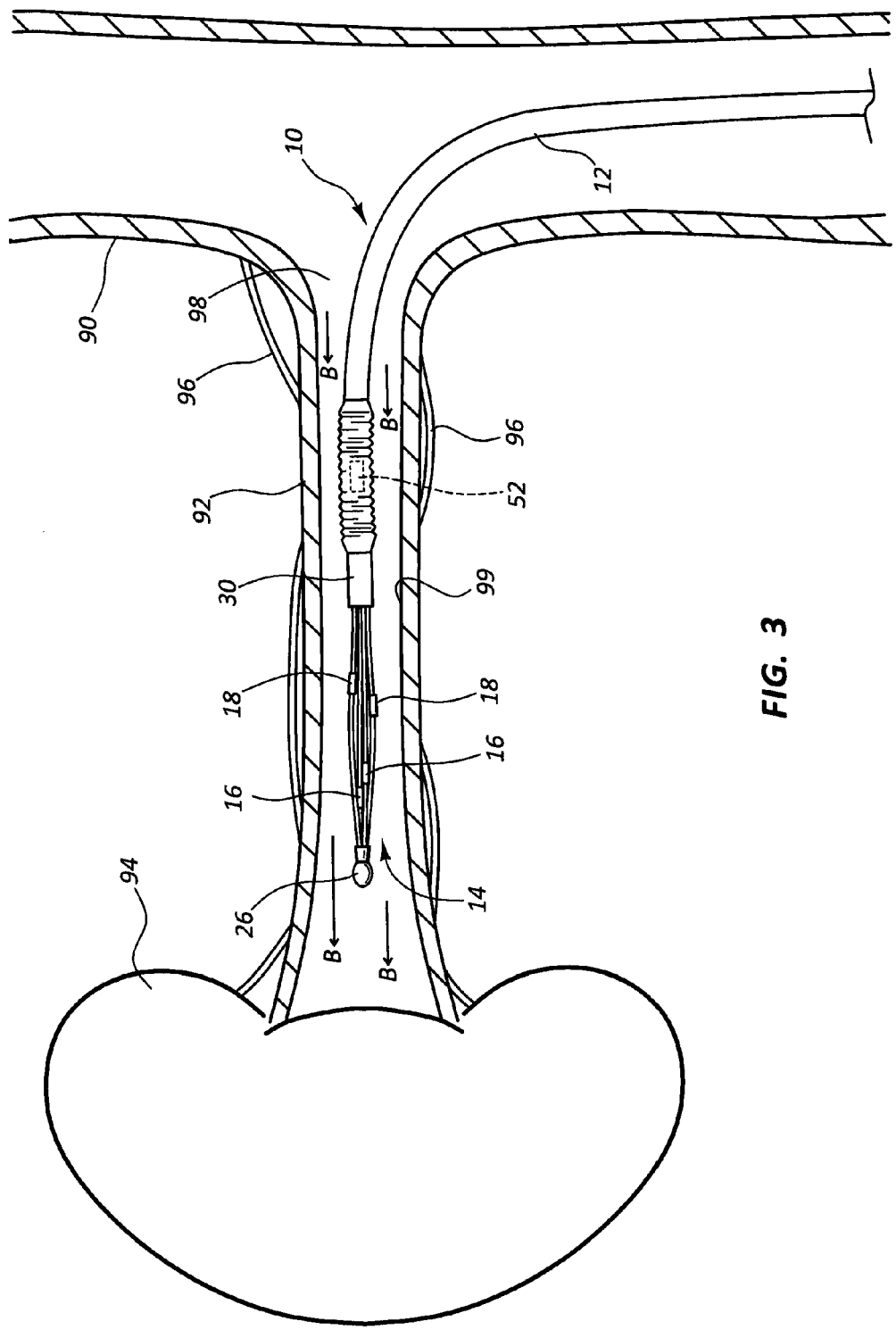
FIG. 3 shows the renal denervation catheter of FIG. 1 positioned in a renal artery.

Referring to FIGS. 3-8, an example method of renal denervation is shown and described. FIG. 3 shows the renal denervation catheter 10 inserted through an aorta 90 and into a renal artery 92. The renal artery 92 provides blood flow to kidney 94. A plurality of renal nerves 96 may extend along an exterior of the renal artery 92 and may be positioned in and on a side wall of the renal artery 92. The renal artery 92 may have an inner surface 99 and may have an ostium 98 leading from the aorta 90.

In an initial step of the renal denervation procedure, the renal denervation catheter 10 may be inserted into the renal artery 92 to position the deployable basket 14 adjacent to the ostium 98. The deployable basket 14 may be operated into a deployed position to contact the ablation electrodes 16, 18 in contact with the inner surface 99 of the renal artery 92. The ablation electrodes 16, 18 or other features of the renal denervation catheter 10 may be operated to provide electrical stimulus of the renal nerves 96 (e.g., via control by controller 20 shown in FIG. 4). The electrical stimulus may produce a physiological response in the kidney 94 such as, for example, increased production of certain fluids and chemicals such as rennin. The physiological response of the kidney 94 may be measurable. This measured response may be compared to the physiological response to the kidney 94 being electrically stimulated after completion of the renal denervation procedure.

Referring again to FIG. 3, the deployable basket 14 is contracted and the renal denervation catheter 10 is further advanced into the renal artery 92. The pressure sensor 26 may begin to measure the blood pressure within renal artery 92. The blood pressure may be plotted on a graph such as the graph shown in FIG. 14A. The blood pressure within the renal artery 92 may be calculated as a mean arterial pressure (MAP).

Figure 4:
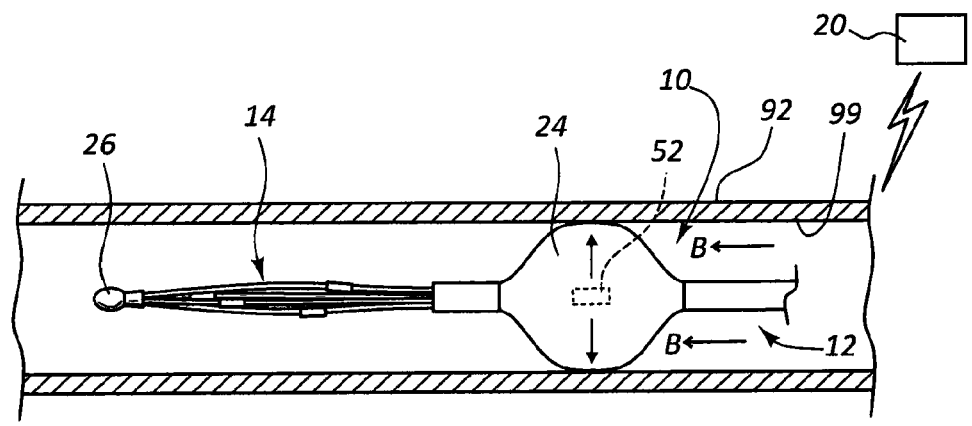
FIG. 4 shows the renal denervation catheter of FIG. 3 with a inflation balloon inflated to block blood flow through the renal artery.
Figure 14A:
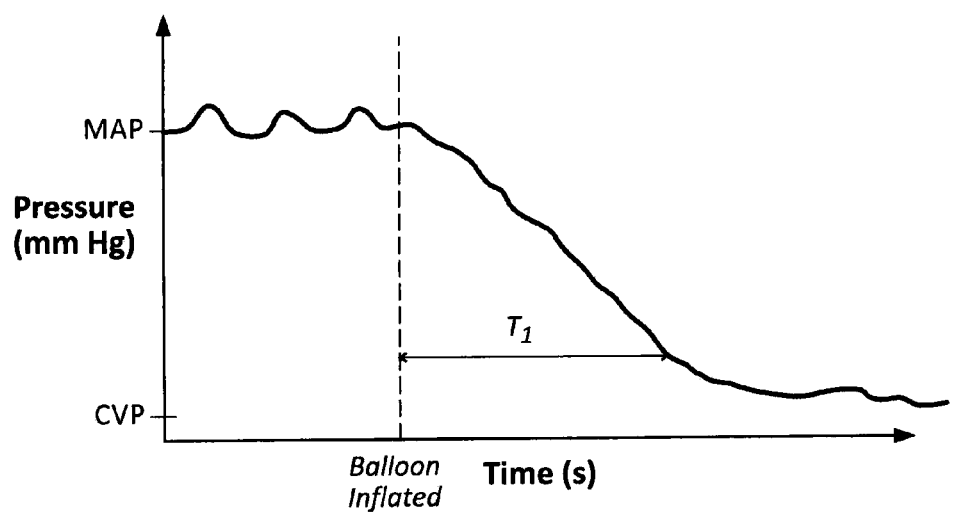
FIGS. 14A and 14B are graphs showing pressure decay within the renal artery distal of an inflated balloon before and after a renal denervation procedure, respectively.

Referring now to FIG. 4, the balloon 24 may be inflated to stop the blood flow B at a location proximal of the pressure sensor 26. Blood in the renal artery 92 distal of the inflated balloon 24 passes to the glomerular apparatus and tubules of the kidney 94 resulting in a reduction in blood pressure. The decrease in renal artery blood pressure distal of the inflated balloon 24 may be modeled as an exponential decay from MAP as shown in FIG. 14A. The blood pressure eventually reaches an asymptotic value or central venous pressure (CVP). A time $T_1$ to complete a percentage of the transition from MAP to CVP is determined using, for example, the controller 20. In one example, the percentage used for determining time $T_1$ is in the range of about 50% to about 75%, and more particularly in the range of about 60% to about 65%. A sigmoidal function or other appropriate choice of curve may be used as a model of the decrease in blood pressure as part of comparing how the rate of decrease in blood pressure changes as a result of the denervation procedure.

Figure 5:
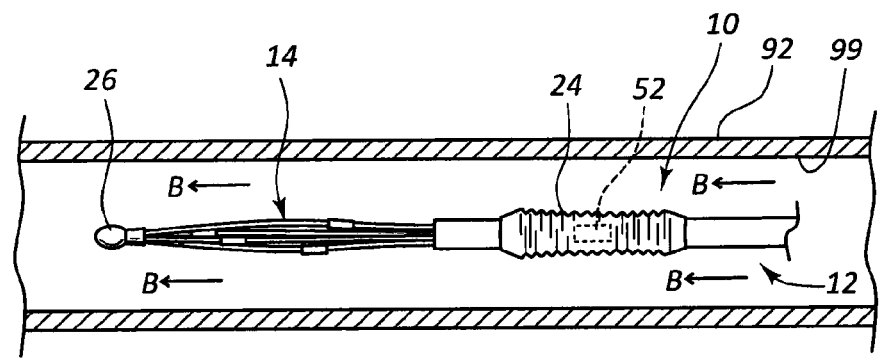
FIG. 5 shows the renal denervation catheter of FIG. 4 with the balloon in a deflated position.
Figure 6:
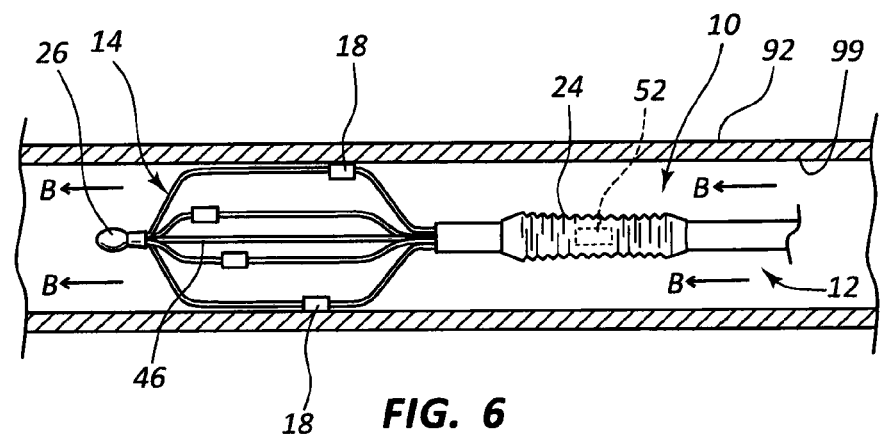
FIG. 6 shows the renal denervation catheter of FIG. 5 in a deployed position within the renal artery.

Referring to FIG. 5, the balloon 24 is deflated and blood flow B is reinitiated in the renal artery 92. Referring to FIG. 6, the deployable basket 14 is deployed to contact the ablation electrodes 16, 18 against the inner surface 99 of the renal artery 92. Power is supplied to the ablation electrodes 16, 18 to ablate the renal artery 92, thereby providing denervation of the renal nerves 96. The pressure sensor 26 may continue to measure the blood pressure during and after completion of the ablation.

Figure 7:
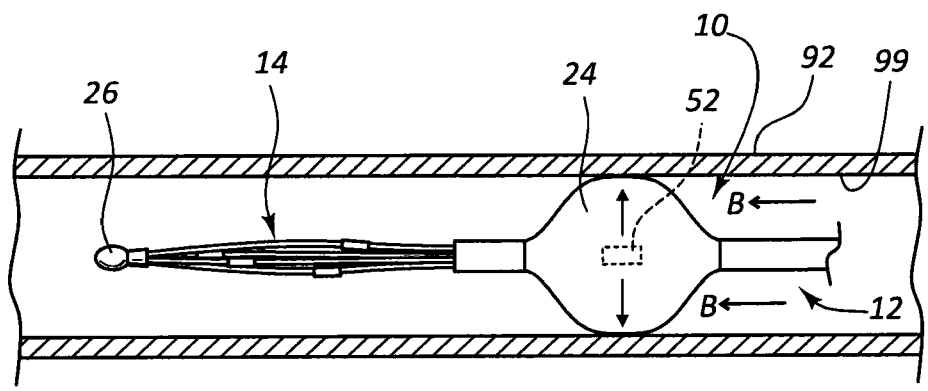
FIG. 7 shows the renal denervation catheter of FIG. 6 in a contracted position and the balloon reinflated to block blood flow through the renal catheter.
Figure 14B:
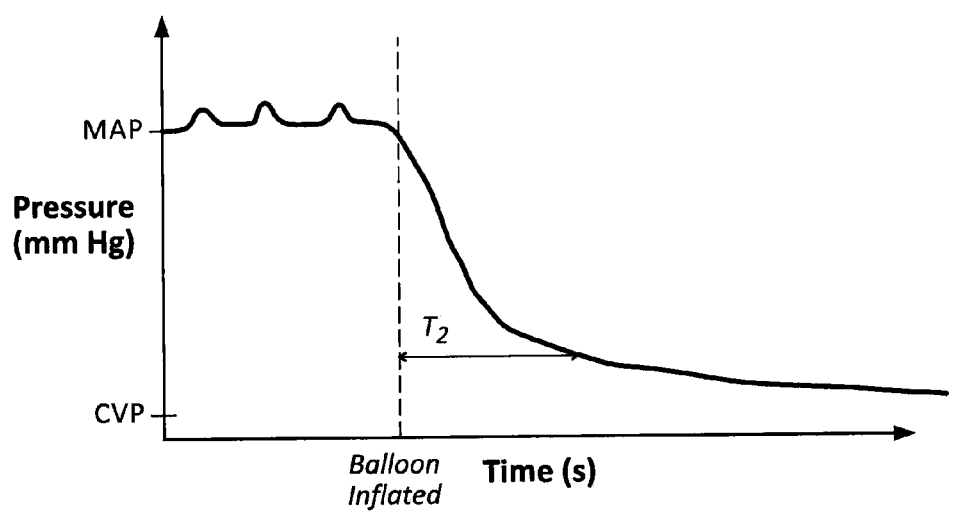

Referring to FIG. 7, the balloon 24 may be reinflated to stop the blood flow B in the renal artery 92. The deployable basket 14 may remain in the deployed position shown in FIG. 6 while the balloon 24 is reinflated. Alternatively, the deployable basket 14 may be contracted as shown in FIG. 7 while the balloon 24 is reinflated. The pressure measurements taken by pressure sensor 26 may be plotted on a graph as shown in FIG. 14B after completion of the denervation described with reference to FIG. 6 and prior to and after reinflating the balloon 24. A time $T_2$ to reach a percentage of the transition from MAP to CVP (e.g., about 63.2%) may be determined using, for example, the controller 20. The time $T_2$ may be compared to the time $T_1$. If the difference between time $T_2$ and time $T_1$ (e.g., $\Delta T$) is within a predetermined range, or the time $T_2$ reaches a predetermined threshold level, the denervation procedure described with reference to FIG. 6 may be considered successful. If the $\Delta T$ or value of $T_2$ is outside of a desired range or does not reach a predetermined value, respectively, the operator may choose to conduct additional ablation.

In one example, the operator deflates the balloon 24, repositions the deployable basket 14 at a different axial position along the renal artery 92, and then further ablates the renal nerves with the ablation electrodes 16, 18. Thereafter, the balloon 24 is reinflated and the pressure sensor 26 supplies a downstream pressure measurement so that an additional pressure decay curve may be plotted in a graph comparable to the graphs shown in FIGS. 14A and 14B. A time $T_3$ to reach a percentage of the transition from MAP to CVP is determined and compared to the time $T_1$ and/or time $T_2$ to determine whether sufficient denervation has occurred.

The pattern of determining a pressure decay curve, evaluating the $\Delta T$ and/or absolute value of $T_2$ or $T_3$, and performing denervation via ablation with ablation electrodes 16, 18 may continue until the operator concludes that sufficient denervation has occurred.

In general, if the pressure decay is sufficiently different after an ablation is performed and/or is indicative of a dilated vessel, the renal denervation procedure may be stopped. Otherwise, another site may be ablated or more energy applied at the same ablation site. The time constant of pressure decay may be a quantitative, acutely changing metric that provides real-time feedback for titration of renal artery ablation. The time constants of contralateral renal arteries may also be compared simultaneously.

Referring now to FIGS. 10-13, another example renal denervation system is shown and described. The renal denervation system includes a renal denervation catheter 100 and a balloon catheter 128, which together may be referred to as a renal denervation system. The renal denervation catheter 100 includes a catheter shaft 112, a deployable basket 114, ablation electrodes 116, 118, a controller 120, and a hub 122. The balloon catheter 128 includes a balloon 124 and a pressure sensor 126. The renal denervation catheter 100 and balloon catheter 128 may be operable independent of each other. For example, the renal denervation catheter 100 may be advanced into and removed from the renal artery 92 independent of advancing and withdrawing the balloon catheter 128.

Figure 10:
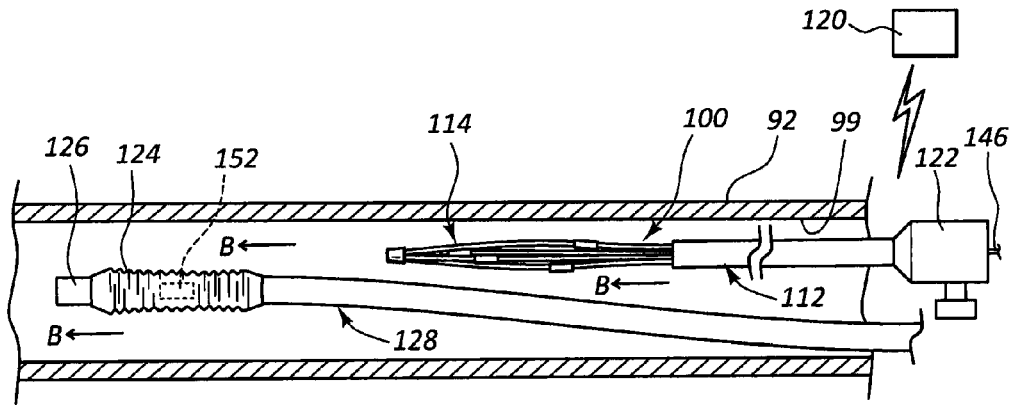
FIG. 10 shows another example renal denervation catheter and a separate balloon catheter positioned in a renal artery in accordance with the present disclosure

Referring to FIG. 10, the balloon catheter 128 and renal denervation catheter 100 may be advanced into the renal artery 92, with the balloon 124 positioned distal of the deployable basket 114. The pressure sensor 126 may be positioned on the balloon catheter 128 at a location distal of the balloon 124 so that the pressure sensor 126 is arranged downstream of the balloon 124 when inflated.

Figure 11:
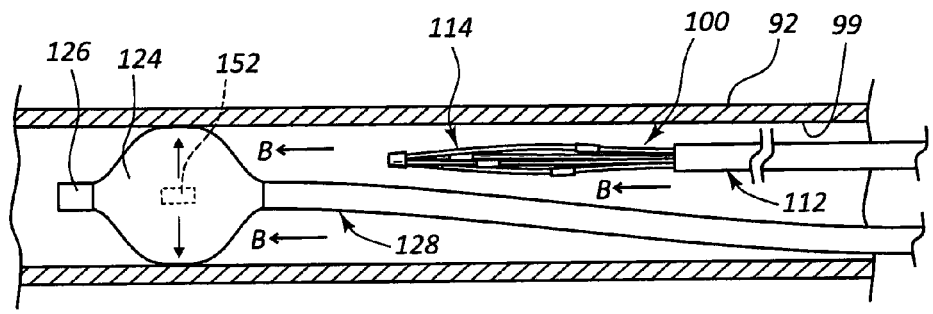
FIG. 11 shows the renal denervation catheter and balloon catheter of FIG. 10 with the balloon inflated to block blood flow within the renal artery.

Referring to FIG. 11, the balloon 124 is inflated to block blood flow B through the renal artery 92. The pressure sensor 126 may collect blood pressure measurements prior to and after inflating the balloon 124. The measurements from pressure sensor 126 may be plotted on a graph such as the graph shown in FIG. 14A. A time $T_1$ may be determined for completion of a percentage of the transition from MAP to CVP (e.g., about 63.2%).

Figure 12:
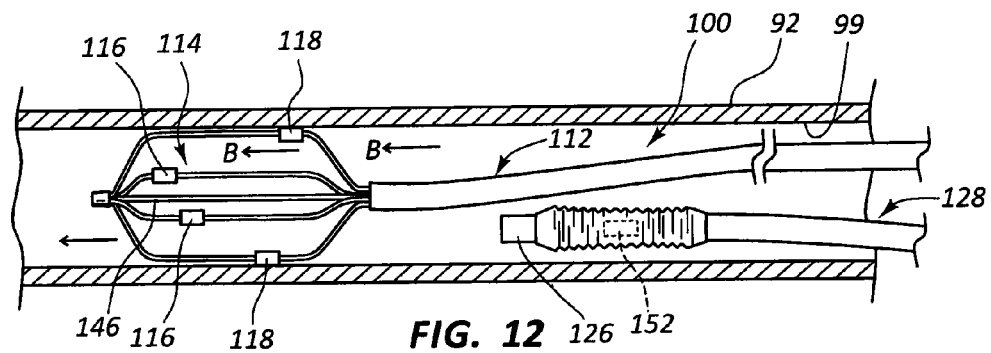
FIG. 12 shows the renal denervation catheter and balloon catheter of FIG. 11 with the balloon deflated and withdrawn and the renal denervation catheter in a deployed position.

Referring to FIG. 12, the balloon 124 is deflated and the balloon catheter 128 is withdrawn to position the balloon 124 proximal of the deployable basket 114. Alternatively, the renal denervation catheter 100 may be advanced while the balloon catheter 128 maintains a constant axial position. The deployable basket 114 may be operated into a deployed position using a pull wire 146 to contact the ablation electrodes 116, 118 against an inner surface 99 of the renal artery 92. The ablation electrodes 116, 118 are operated to ablate the renal nerves 96 associated with the renal artery 92. The controller 120 may operate to control operation of at least the ablation electrodes 116, 118. Blood flow B may continue after deflating the balloon 124 and during and after the denervation procedure.

Figure 13:
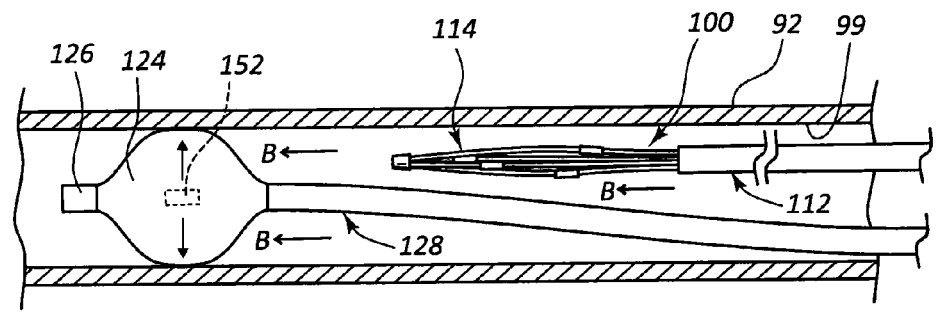
FIG. 13 shows the renal denervation catheter and balloon catheter of FIG. 12 with the renal denervation catheter in a contracted position and the balloon catheter advanced with the balloon inflated to block blood flow through the renal artery.

Referring to FIG. 13, the balloon 24 may be positioned distal of the deployable basket 114 and then inflated to stop the blood flow B. The pressure sensor 126 may determine blood pressure at a location distal of the balloon 124 prior to and after inflation of balloon 124. The measurements from pressure sensor 126 may be plotted on a graph such as the graph shown in FIG. 14B. A time $T_2$ to reach a percentage of the transition from MAP to CVP (e.g., about 63%) may be determined and compared to the time $T_1$. If the $\Delta T$ between $T_2$ and $T_1$ is within a predetermined range, or the value of $T_2$ reaches a threshold value, the renal denervation procedure may be stopped. If the $\Delta T$ is outside of a certain range, or the absolute value of $T_2$ does not meet the threshold level, the operator may choose to perform additional ablation and denervation.

The steps shown and described with reference to FIGS. 10-13 may be repeated as needed until a desired $\Delta T$ is reached. The renal denervation catheter 100 and balloon catheter 128 may be advanced and withdrawn axially as needed in order to position the balloon 124 at a location where blood flow B is stopped when a balloon 124 is inflated.

As mentioned above, in some examples, rather than using $\Delta T$ as the primary indicator of efficacy of the denervation procedure, an absolute value for T may be used. For example, a value of T less than 5 seconds may indicate sufficient denervation has occurred.

Referring again to FIGS. 3-8, another example method of renal denervation is described using the renal denervation catheter 10. The renal denervation catheter 10 may be operable in this method without the use of pressure sensor 26. According to this method, an amount of time required to fill the balloon 24 to a predetermined pressure is used to determine sympathetic tone in the renal artery 92, which may correlate with efficacy of a renal denervation procedure. Referring to FIG. 3, the renal denervation catheter 10 may be positioned within the renal artery 92. FIG. 4 shows the balloon 24 inflated. The time required to fill the balloon 24 to a predetermined pressure, size or shape is measured. In one example, a balloon sensor 52 may be used to determine the pressure within balloon 24. The balloon sensor 52 may be positioned within balloon 24 or may be positioned at any desired location along the flow path of the inflation fluid used to fill balloon 24. In one example, the balloon sensor 52 is associated with the source of inflation fluid, which is connected to the inflation port 50 of the hub 22.

Referring to FIG. 5, the balloon 24 is deflated and the renal denervation catheter 10 is operated to deploy the deployable basket 14 to contact the ablation electrodes 16, 18 against the inner surface 99 of the renal artery 92. The ablation electrodes 16, 18 are operated to ablate the renal nerves 96 associated with the renal artery 92. After completing the ablation, the balloon 24 is reinflated as shown in FIG. 7. An amount of time required to fill the balloon 24 (e.g., reach a threshold pressure condition within balloon 24 or achieve a certain size or shape) is determined and compared to the amount of time required to fill the balloon 24 prior to ablation. If the denervation procedure achieved its therapeutic aim of unloading sympathetic tone from the renal arterioles and capillaries, the resistive portion of the vascular impedance will decrease, while the material elasticity of the renal artery 92 will not change substantially. If the renal denervation procedure is effective and vasodilation ensues, the time to inflate the balloon 24 decreases. The balloon 24 may be inflated and a time recorded prior to the procedure and then again after each ablation at various sites along the renal artery. If the time to fill the balloon 24 decreases sufficiently after ablation (e.g., a $\Delta T$ within a predetermined range), the renal denervation procedure may be stopped. Alternatively, as mentioned above, an absolute value for T may be used to determine whether sufficient denervation has occurred. If the operator determines additional denervation is required, another site may be ablated or more energy may be applied at the same ablation site. As shown in FIG. 8, the balloon 24 may eventually be deflated, the deployable basket 14 contracted, and the renal denervation catheter 100 removed from the renal artery 92.

Referring again to FIGS. 10-13, the renal denervation catheter 100 and balloon catheter 128 may be used to determine the efficacy of a renal denervation procedure based on the amount of time required to fill the balloon 124. The renal denervation catheter 100 and balloon catheter 128 may be positioned in the renal artery 92 as shown in FIG. 10. The balloon 124 is inflated prior to ablation using the renal denervation catheter 100. The time required to inflate the balloon 124 to a predetermined pressure is determined as shown in FIG. 11. The pressure conditioned within balloon 124 may be determined using a balloon sensor 152. Alternatively, other devices and methods may be used to determine whether a size, shape or other feature or characteristic of the balloon has been achieved. Thereafter, the balloon 124 is deflated and the balloon catheter 128 is positioned proximal of the deployable basket 114. The renal denervation catheter 100 is operated to ablate the renal artery 92.

After the ablation, the balloon 124 is again positioned distal of the renal denervation catheter 100 and inflated. The time required to inflate the balloon 124 to a predetermined pressure or to reach a desired shape or size is determined and compared to the time required to fill the balloon 124 prior to the denervation procedure (e.g., determination of ΔT). If the amount of time required to fill the balloon 124 to the predetermined pressure decreases a sufficient amount or is completed in a predetermined time period, the operator may stop the renal denervation procedure and remove the renal denervation catheter 100 and balloon catheter 128 from the renal artery 92. Otherwise, another site may be ablated or more energy may be applied to the same ablation site to conduct further denervation. Thereafter, the balloon 124 is again inflated and the time required to fill the balloon 124 is compared to at least one of the times required to fill the balloon previously (e.g., before or after previous ablations).

The methods of determining efficacy of a renal denervation procedure using the time required to fill a balloon described above may be based primarily on vascular impedance. Vascular impedance presents as a resistance, determined primarily by a sympathetic tone, along with a portion that depends on vascular distention as a function of fluid volume and the elastic material properties of the containing vessels. Successful renal denervation may change vascular impedance.

The amount of time required to fill the inflation balloon may be referred to as a performance characteristic of the balloon. Other performance characteristics of the balloon may be used as an indicator of vascular impedance or other characteristics of the renal artery such as sympathetic tone.

As used in this specification and the appended claims, the terms "engage" and "engagable" are used broadly to mean interlock, mesh, or contact between two structures or devices. A "tube" is an elongated device with a passageway. A "lumen" refers to any open space or cavity in a bodily organ, especially in a blood vessel. The words "including" and "having," as well as their derivatives, as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A method of determining efficacy of a renal denervation procedure in a renal artery, comprising:
   providing a renal denervation catheter and an inflation balloon;
   measuring a first amount of time to fill the inflation balloon within the renal artery;
   deflating the inflation balloon;
   performing a first renal denervation procedure in the renal artery with the renal denervation catheter;
   after performing the renal denervation procedure, measuring a second amount of time to fill the inflation balloon within the renal artery;
   comparing the first and second amounts of time to determine a change in the first and second amounts of time; and
   determining that the efficacy of the first renal denervation procedure is sufficient when the change in the first and second amounts of time is within a predetermined range.

2. The method of claim 1, wherein measuring the first amount of time to fill the inflation balloon includes measuring the first amount of time to fill the inflation balloon to a predetermined pressure level.

3. The method of claim 1, further comprising:
   determining that the efficacy of the first renal denervation procedure is insufficient when the change in the first and second amounts of time is not within the predetermined range;
   axially moving the renal denervation catheter within the renal artery;
   performing a second renal denervation procedure;
   after performing the second renal denervation procedure, measuring a third amount of time to fill the inflation balloon; and
   comparing the third amount of time with at least one of the first and second amounts of time to determine efficacy of the second renal denervation procedure.

4. The method of claim 3, wherein comparing the third amount of time with at least one of the first and second amounts of time comprises comparing the first and third amounts of time to determine a change in the first and third amounts of time, the method further comprising determining that the efficacy of the second renal denervation procedure is sufficient when the change in the first and third amounts of time is within the predetermined range.

5. The method of claim 3, wherein comparing the third amount of time with at least one of the first and second amounts of time comprises comparing the second and third amounts of time to determine a change in the second and third amounts of time, the method further comprising determining that the efficacy of the second renal denervation procedure is sufficient when the change in the second and third amounts of time is within another predetermined range.

6. The method of claim 1, further comprising positioning a balloon sensor in the inflation balloon, wherein measuring the first amount of time comprises measuring the first amount of time using the balloon sensor, and wherein measuring the second amount of time comprises measuring the second amount of time using the balloon sensor.

7. The method of claim 1, wherein the change between the first amount of time and the second amount of time correlates to unloading of sympathetic tone from the renal artery.

8. The method of claim 1, wherein measuring the first amount of time to fill the inflation balloon includes measuring the first amount of time to fill the inflation balloon to a predetermined size.

9. The method of claim 1 further comprising removing the renal denervation catheter and the inflation balloon from the renal artery after determining that the efficacy of the first renal denervation procedure is sufficient.

10. The method of claim 1 further comprising providing the renal denervation catheter and inflation balloon on a common delivery device.

11. A renal denervation system, comprising:

an ablation catheter insertable into a renal artery to perform a renal denervation procedure including ablating a renal artery;

an inflation balloon inflatable within the renal artery, wherein a performance characteristic of the inflation balloon indicates efficacy of the renal denervation procedure, wherein the performance characteristic of the inflation balloon includes an amount of time to fill the inflation balloon; and a balloon sensor within the inflation balloon, the balloon sensor configured to measure a first amount of time to fill the inflation balloon before ablating the renal artery and a second amount of time to fill the inflation balloon after ablating the renal artery to detect a change in the first and second amounts of time.

12. The renal denervation system of claim 11, wherein the first amount of time to fill the inflation balloon includes the first amount of time to fill the inflation balloon to a predetermined pressure level.

13. The renal denervation system of claim 11, wherein the change between the first amount of time and the second amount of time correlates to unloading of sympathetic tone from the renal artery.

14. The renal denervation system of claim 11, wherein the first amount of time to fill the inflation balloon includes the first amount of time to fill the inflation balloon to a predetermined size.

15. The renal denervation system of claim 11, wherein the renal denervation catheter and the inflation balloon are coupled to a common delivery device.

16. An inflation balloon configured to be inflated within a renal artery as part of a renal denervation procedure including ablating the renal artery, wherein a performance characteristic of the inflation balloon indicates efficacy of the renal denervation procedure, wherein the performance characteristic of the inflation balloon includes an amount of time to fill the inflation balloon, the inflation balloon comprising a balloon sensor, the balloon sensor configured to measure a first amount of time to fill the inflation balloon before ablating the renal artery and a second amount of time to fill the inflation balloon after ablating the renal artery to detect a change in the first and second amounts of time.

17. The inflation balloon of claim 16, wherein the first amount of time to fill the inflation balloon includes the first amount of time to fill the inflation balloon to a predetermined pressure level.

18. The inflation balloon of claim 16, wherein the first amount of time to fill the inflation balloon includes the first amount of time to fill the inflation balloon to a predetermined size.

* * * * *